US011357686B2

(12) United States Patent
Breegi et al.

(10) Patent No.: US 11,357,686 B2
(45) Date of Patent: *Jun. 14, 2022

(54) DEPLOYABLE COMPACT SURGICAL AND BIOLOGICAL APPARATUS AND METHODS OF USE

(71) Applicant: BREEGI SCIENTIFIC, INC., Woburn, MA (US)

(72) Inventors: Wisam K. Breegi, Woburn, MA (US); Robert Sykes, Burlington, MA (US)

(73) Assignee: BREEGI SCIENTIFIC, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/272,467

(22) Filed: Feb. 11, 2019

(65) Prior Publication Data
US 2020/0337922 A1 Oct. 29, 2020

Related U.S. Application Data

(63) Continuation of application No. 14/947,079, filed on Nov. 20, 2015, now Pat. No. 10,251,801, which is a
(Continued)

(51) Int. Cl.
*A61G 10/00* (2006.01)
*A61B 90/40* (2016.01)
(Continued)

(52) U.S. Cl.
CPC ............ *A61G 10/005* (2013.01); *A61B 46/00* (2016.02); *A61B 90/30* (2016.02); *A61B 90/40* (2016.02);
(Continued)

(58) Field of Classification Search
CPC ............ A61G 10/04; A61G 10/00–026; A61G 11/00–009; A61B 90/40; A61B 2090/401
See application file for complete search history.

(56) References Cited

U.S. PATENT DOCUMENTS 2,473,033 A 6/1949 Letag
2,699,775 A * 1/1955 Cameto .................. A61G 10/04
128/205.26
(Continued)

FOREIGN PATENT DOCUMENTS

CN 103796623 A 2/2017
JP 08191866 A * 7/1996
(Continued)

OTHER PUBLICATIONS

English translation of Watanabe (Year: 1996).*
(Continued)

*Primary Examiner* — Thaddeus B Cox
(74) *Attorney, Agent, or Firm* — Nixon Peabody LLP; David S. Resnick; Susanna C. Benn (57) ABSTRACT

A collapsible containment apparatus (36) with a first hub (21), a second hub (22), a plurality of articulated arms (23, 25) coupled to the first hub (21), a plurality of support arms (24) coupled to both the second hub (22) and the articulated arms (23), and a flexible canopy (73) carried by the articulated arms (23). The apparatus (36) is collapsed by relative movement of the two hubs (21, 22) away from one another, and deployed by relative movement of the hubs (21, 22) toward one another. When the apparatus (36) is deployed the canopy (73) creates a closed interior environment, which may be sterile.

17 Claims, 10 Drawing Sheets

Related U.S. Application Data continuation of application No. PCT/US2014/038698, filed on May 20, 2014.

(60) Provisional application No. 61/825,474, filed on May 20, 2013.

(51) Int. Cl.

| | | |
|---|---|---|
| *A61G 10/02* | (2006.01) | |
| *A61B 46/00* | (2016.01) | |
| *A61G 11/00* | (2006.01) | |
| *A61G 13/10* | (2006.01) | |
| *A61F 7/00* | (2006.01) | |
| *A61B 90/30* | (2016.01) | |
| *A61G 7/057* | (2006.01) | |

(52) U.S. Cl.
CPC ............ *A61F 7/0053* (2013.01); *A61G 10/02* (2013.01); *A61G 11/009* (2013.01); *A61G 13/108* (2013.01); *A61G 7/05769* (2013.01)

(56) References Cited

U.S. PATENT DOCUMENTS

| | | | |
|---|---|---|---|
| 2,915,074 A | 12/1959 | Cameto | |
| 3,000,379 A * | 9/1961 | Viers | A61G 10/04 128/204.16 |
| 3,710,791 A * | 1/1973 | Deaton | A61G 11/00 128/205.26 |
| 3,850,172 A | 11/1974 | Cazalis | |
| 4,000,749 A * | 1/1977 | Busco | A61G 10/005 600/21 |
| 4,077,417 A | 3/1978 | Beavers | |
| 4,275,719 A | 6/1981 | Mayer | |
| 4,367,728 A | 1/1983 | Mutke | |
| 4,407,280 A * | 10/1983 | Trammell | A61M 16/06 128/205.19 |
| 4,550,713 A * | 11/1985 | Hyman | A61F 9/007 128/849 |
| 4,612,916 A | 9/1986 | Akers et al. | |
| 4,950,222 A | 8/1990 | Scott et al. | |
| 4,939,803 A | 10/1990 | Waters | |
| 5,061,235 A | 10/1991 | Hogan | |
| 5,113,854 A * | 5/1992 | Dosch | A62B 7/08 128/201.23 |
| 5,316,541 A * | 5/1994 | Fischer | A61G 10/005 128/849 |
| 5,333,634 A | 8/1994 | Taylor | |
| 5,342,121 A * | 8/1994 | Koria | A61G 10/005 312/1 |
| 5,495,857 A * | 3/1996 | Fegan | A61G 10/02 128/848 |
| 5,728,041 A | 3/1998 | Fowler, Jr. | |
| 6,001,057 A * | 12/1999 | Bongiovanni | A61G 1/04 5/629 |
| 6,217,099 B1 | 4/2001 | McKinney | |
| 6,321,764 B1 * | 11/2001 | Gauger | A61G 1/0212 135/128 |
| 6,354,316 B1 | 3/2002 | Chen | |
| 6,367,476 B1 | 4/2002 | Conn | |
| 6,418,932 B2 | 7/2002 | Paschal, Jr. et al. | |
| 6,461,290 B1 * | 10/2002 | Reichman | A61G 10/005 5/312 |
| 6,500,111 B1 | 12/2002 | Salmon | |
| 6,508,850 B1 * | 1/2003 | Kotliar | A61G 10/005 55/385.2 |
| 7,406,978 B2 | 8/2008 | Mintie et al. | |
| 7,481,234 B1 | 1/2009 | Gustafson et al. | |
| 7,503,890 B2 | 3/2009 | Kubicsko et al. | |
| 7,818,835 B2 | 10/2010 | Heaton et al. | |
| 8,245,713 B2 | 8/2012 | Paschal, Jr. et al. | |
| 2001/0029955 A1 * | 10/2001 | Paschal, Jr. | A61G 10/005 128/846 |
| 2002/0045796 A1 * | 4/2002 | O'Connor | A61B 90/40 600/21 |
| 2002/0147381 A1 | 10/2002 | Kolarovic | |
| 2004/0133064 A1 | 7/2004 | Castillon Levano et al. | |
| 2005/0097829 A1 | 5/2005 | Seo | |
| 2006/0247487 A1 | 11/2006 | Arts et al. | |
| 2007/0056593 A1 * | 3/2007 | Kubicsko | B08B 15/026 128/846 |
| 2007/0151588 A1 | 7/2007 | Yul et al. | |
| 2008/0041399 A1 * | 2/2008 | Kriek | A61B 90/40 128/852 |
| 2008/0284289 A1 | 11/2008 | Fisher | |
| 2009/0093671 A1 * | 4/2009 | Maloney | A61G 10/005 600/21 |
| 2010/0044372 A1 | 2/2010 | Kournikakis et al. | |
| 2011/0192438 A1 | 8/2011 | Chin et al. | |
| 2012/0215054 A1 | 8/2012 | Rodrigues | |
| 2013/0074895 A1 | 3/2013 | Zimmer | |
| 2014/0163326 A1 * | 6/2014 | Forsell | A61B 90/40 600/207 |
| 2014/0212329 A1 | 7/2014 | Veen et al. | |
| 2014/0316455 A1 | 10/2014 | Gnanashanmugam et al. | |
| 2016/0074268 A1 | 3/2016 | Breegi et al. | |

FOREIGN PATENT DOCUMENTS

| | | |
|---|---|---|
| WO | 2005009316 A1 | 2/2005 |
| WO | 2015/189541 A1 | 12/2015 |

OTHER PUBLICATIONS

The International Preliminary Report on Patentability dated Nov. 24, 2015 for corresponding PCT Applicaiton No. PCT/US2014/038698.

* cited by examiner

DEPLOYABLE COMPACT SURGICAL AND BIOLOGICAL APPARATUS AND METHODS OF USE

CROSS-REFERENCE TO RELATED APPLICATION

This application is a continuation of U.S. patent application Ser. No. 14/947,079, filed on 20 Nov. 2015, now U.S. Pat. No. 10,251,801, which is a continuation of International Patent Application PCT/US2014/038698, filed on 20 May 2014, which claims the benefit under § 119(e) of U.S. Provisional Patent Application Ser. No. 61/825,474, filed May 20, 2013, the disclosure of which are each incorporated herein in their entireties by reference.

FIELD

The present invention relates to a portable designated work station.

BACKGROUND

Containment of an isolated sterile environment and controlled processes within the environment are central ideas behind having a deployable compact surgical and biological apparatus and methods of use. One application for the apparatus is to perform surgical, medical and non-medical procedures with post-operation capability. Current systems spaces have limitations; they are large, not collapsible, limited in number, stationary, and must contain the patient's entire body, even in mobile medical units. In addition to these limitations, and in spite of these sterile precautions, nosocomial infections due to cross-contamination and exposure to exogenous or endogenous airborne contaminants are still very high. There is a need for a sterile controlled microenvironment. In larger scale emergencies, battlefields, and areas of conflict, mobile field treatment units and other disaster response surgical field units are widely used in spite of their limitations of number, locations, size, cost and time of deployment and limitation of functions. After initial treatment there is a need for post-surgical care facilities for large wounds, amputations and burns. More often, specific wound treatment and healing, such as skin grafting treatment, may require specific procedures and highly specialized facilities for treatment and containment, one of which is hyperbaric oxygen therapy (HBOT). HBOT chambers are large, complex to use, expensive to manufacture and assemble, and require specific medical facilities. These chambers are often used for limited time periods for diabetic wounds and persistent wound infection treatment. All of these treatments require the placement of the patient entirely within a controlled space with limited access for direct treatment, and an expensive hospitalization with the presence of an aseptic environment; which are limited and hard to maintain. Such contained spaces are not always available, are limited in numbers and are expensive.

An immediate step is wound control, preparation and treatment, while post-care and healing comprise a longer term step. During these processes, medical dressings are not able to contain the wound while keeping it directly accessible for monitoring to the care provider. Bandages and liquid dressings may trap foreign contaminants in the wound, and may not prevent further contamination. Therefore, there is a critical need for site accessibility for treatment methods of wound and burn triage, along with containment to help prevent further complications that can lead to undesirable outcomes.

In a wide range of laboratory and industrial settings for biological, chemical, electronic or other special processing needs, there is the need to perform the work in a sterile, aseptic or isolated and contained environment. Special requirements are sometimes overwhelming and costly to achieve.

SUMMARY

Presently there is no solution for an expandable, portable, small, light-weight, inexpensive and optionally sterile microenvironment. The invention solves this problem.

The deployable compact surgical and biological apparatus and methods of use can provide a full or partial solution. The apparatus is an expandable, reversible controlled microenvironment system; it is light and portable, and fits many applications. It meets the individual and diverse tasks in medical, laboratory, and industrial fields. The present invention provides an isolated space or volume which may expand longitudinally to enclose a controlled environment; allows visual observations; allows manipulation, insertion, and/or removal of items within the interior space through one or more particular sleeves; while maintaining an isolated and sealed environment. The device provides either full or partial containment of objects which are contained within, or interface with, the controlled microenvironment.

This invention fulfills the need for a sterile expandable, controllable, small, deployable, portable and practical solution to properly contain and support surgical sites, treatment and healing of wounds, and application of medication and analgesics. In addition the invention will facilitate skin grafting and in-vivo tissue and cell culture, without the loss of wound containment integrity and its surrounding environment sterility. Fully or partially containing the subject for wound treatment within a collapsible apparatus will address the immediate needs of the patient while being easily carried by the medical personnel in their pack. This need is not only required in the secondary care unit but as a primary triage measure to contain the wound as soon as it happens to prevent loss of vital tissues, tissue functions and costly infections. This invention meets these needs, and also can provide a controlled microenvironment to conduct otherwise complex and costly procedures.

In addition, the invention meets the requirements of incubators for various applications. These applications can include neonatal incubators, tissue and cell culture incubators and general biological incubators. Acting as an incubator, the invention can also sterilely isolate, and allow independent manipulation of, different contained items internally without cross-contamination. Each internal compartment can have its own independently controlled microenvironment. The invention meets the requirements of isolated and controlled environments.

The invention can incorporate fluid delivery ports, air-locked bi-directional sleeves and sealing features. It is capable of introducing gases and/or other fluids into the enclosed work space, and can include components and features that control the nature, purity, temperature, humidity, light and/or sterility of gases or other fluids introduced into the enclosed space. These components and features can include pumps, filters, ultraviolet, ozonizer sterilizers, conduits, couplings, canisters, valves, similar fluid control devices, electrical controls, direct and indirect lights (white, ultraviolet, blue or infrared light, etc.) and wiring. The invention can accommodate sealed entry of a variety of devices and device extensions which can be employed to treat wounds, minimize pain, maintain a sterile environment, and other non-medical functions.

One application of the apparatus is to create a contained surgical site in order to provide the means to conduct a surgery. The device is capable of sealing around the perimeter of a partially or fully introduced object. Such contained microenvironment can be achieved through an internal or an external source of sterilization, such as ultraviolet germicidal irradiation or ozonizer that circulates treated air within the microenvironment.

This apparatus consists of an expandable and collapsible containment structure that provides a controlled environment, sized and configured by a plurality of ribs to define a closed contained space and to extend in at least one direction, generally outwardly, with connections and access sleeves for manipulation and handling.

The apparatus may accomplish a reversible expandable microenvironment system comprised of an expandable and collapsible containment frame and membrane (canopy), which is sized and configured to support the contained space, to define this closed space (alternately called contained space, containment space, contained volume, or containment volume). It extends in at least one direction generally outwardly from the space to house a work field of full or partial subject containment. The space is sized to define an operating or containment field, which consists of a combination of a plurality of ribs each comprising a lower portion, and upper portion, and a pivot connector interconnecting the lower and upper portions which makes the containment structure. There can be a variety of mechanisms used to achieve this type of expandable containment space structure, for use in the desired applications. It can be expanded longitudinally to fully enclose longer and/or larger objects.

One aspect may be a collapsible containment apparatus comprising a first hub, a second hub, a plurality of articulated arms coupled to the first hub, a plurality of support arms coupled to both the second hub and the articulated arms, and a flexible canopy carried by the articulated arms. The apparatus is collapsed by relative movement of the two hubs away from one another, and deployed by relative movement of the hubs toward one another. When the apparatus is deployed the canopy creates a closed interior environment.

The apparatus may include a shaft connecting the first and second hubs, where one or both of the hubs are movable along the shaft. The articulated arms may be pivotally coupled to the first hub, and the support arms may be pivotably coupled to both the second hub and the articulated arms. The canopy may be at least in part transparent. The canopy may be made at least in part of a polymeric material. The canopy may include a base that forms the bottom of the interior environment. The base may comprise an outer layer that is impervious to fluids, and at least one layer inside of the outer layer that is constructed and arranged to absorb fluids. There may be an adhesive on the outside of the base, to allow the base to be adhered to an object.

The apparatus may include a light source that provides light to the interior environment. The apparatus may further comprise an ultraviolet (UV) light source that is located so as to expose air in the interior environment to UV light. The UV light source may be located outside of the canopy in a volume that is fluidly coupled to the interior environment. The apparatus may include one or more sleeves coupled to the canopy and extending into the interior, the sleeves sized and shaped to accept the lower end of an arm of a person. The sleeves may comprise an elastic cuff that fits tightly over the lower end of the arm. The apparatus may include an air-lock sleeve coupled to the canopy. The air-lock sleeve may include mechanisms at each end that allow the sleeve to be selectively opened and closed at both ends of the sleeve.

The apparatus may further include a releasable locking device that is engaged when the hubs are moved together. The apparatus may further include a source of heating or cooling fluid that can be passed through a base of the canopy when the apparatus is deployed. The apparatus may further include a pair of flap drapes coupled to the canopy and that can be wrapped around an object. The canopy may include a base that forms the bottom of the interior environment, where the drapes are coupled to this base. The apparatus may comprise two sets of hubs and arms, connected together by hinged struts that allow the two sets of hubs and arms to be pulled apart longitudinally while still supporting the canopy. The apparatus may further include a reinforcement structure for the canopy that is either on or in the canopy. The canopy may have an outer layer that is impervious to fluids. The apparatus may further include one or more tubes that pass through the canopy. The tubes may be for delivery of gas, liquid or mist into the interior environment or into a base of the canopy.

DETAILED DESCRIPTION

Figure 10:
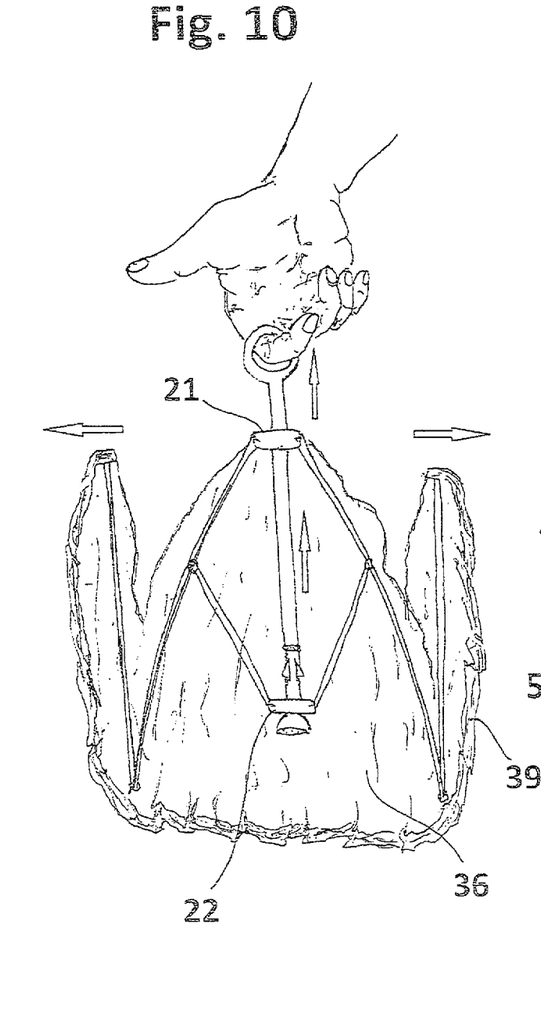
FIG. 10: Deployment of the apparatus
Figures 14, 15, 16:
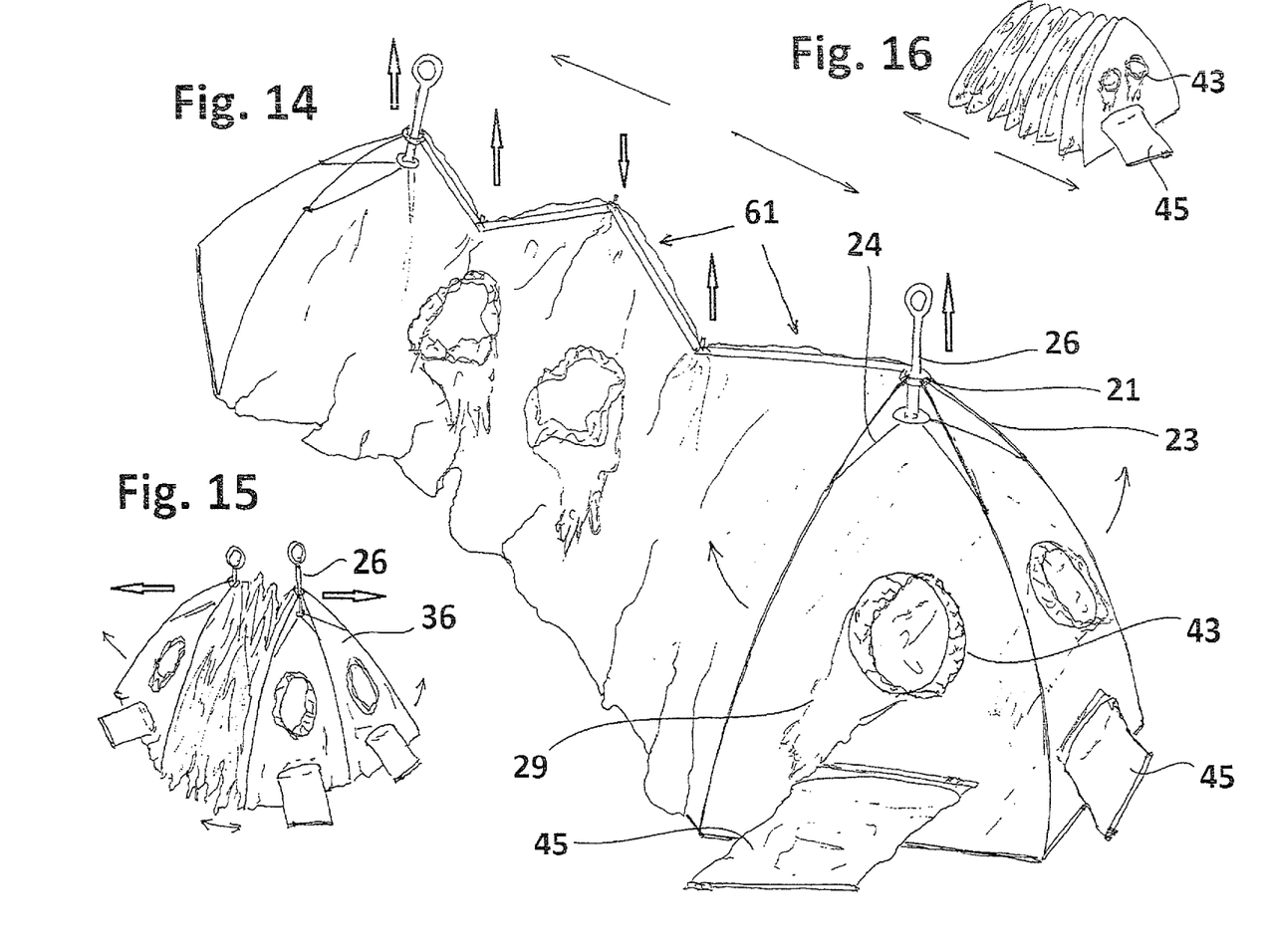
FIG. 14: Example of accordion-like longitudinal expansion configuration
FIG. 15: Non-deployed longitudinal configuration
FIG. 16: Coiled configuration

An object of the present invention is to fulfill the need for a deployable compact surgical and biological apparatus and methods of use. In accordance with the principles of the present invention, this objective is obtained by providing a versatile, portable, expandable, surgical/medical and non-medical contained work space. It includes at least one collapsible container defining a generally geometric-shaped configuration in a sterile sealed package. The package is sized for a portable kit that is easy to carry by individuals. It is constructed and arranged to be expandable from a cylindrical (FIG. 10), longitudinal (FIG. 14,15) or flat (FIG. 16), configuration to a closed space (volume), or custom contoured operative configuration defining a contained (closed) space sufficient to house and conduct any given operation with the ability to have its own microenvironment.

Figures 1, 3:
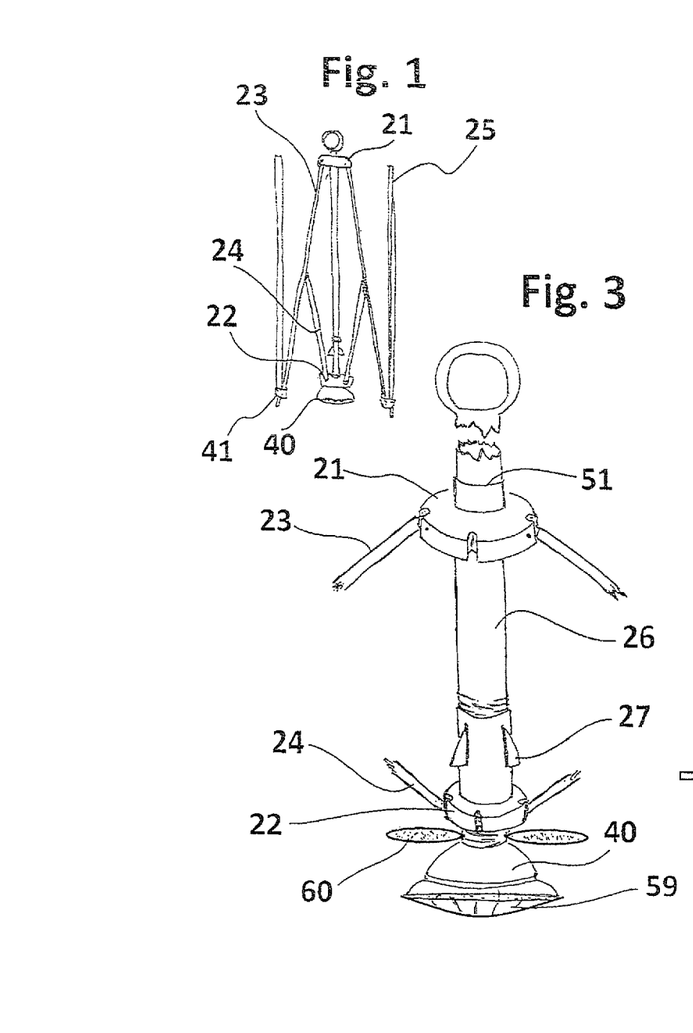
FIG. 1: Collapsible rib frame
FIG. 3: Central shaft with upper and lower clevis (hubs)
Figure 2:
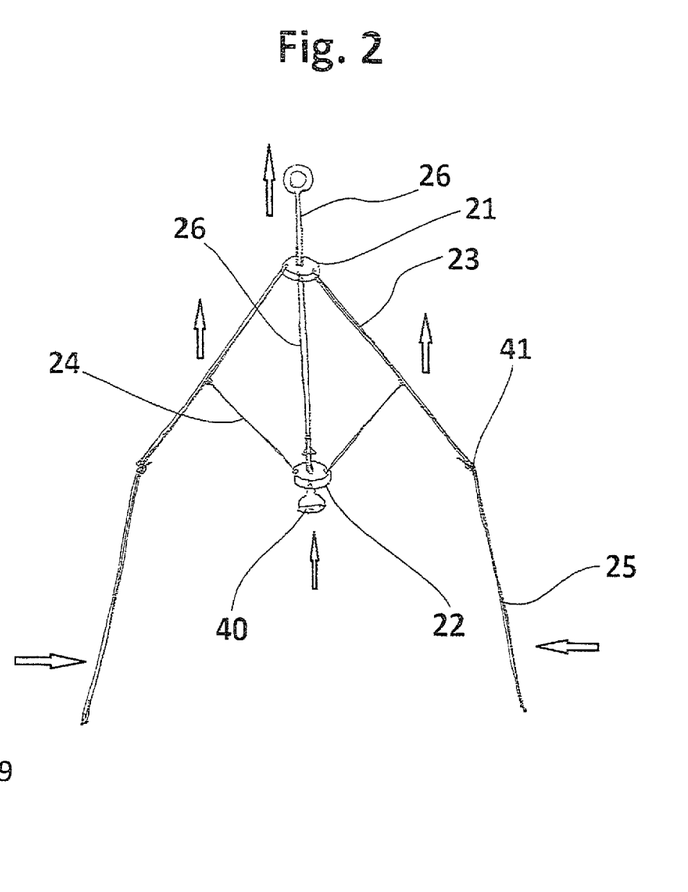
FIG. 2: Partially erected rib frame
Figure 9:
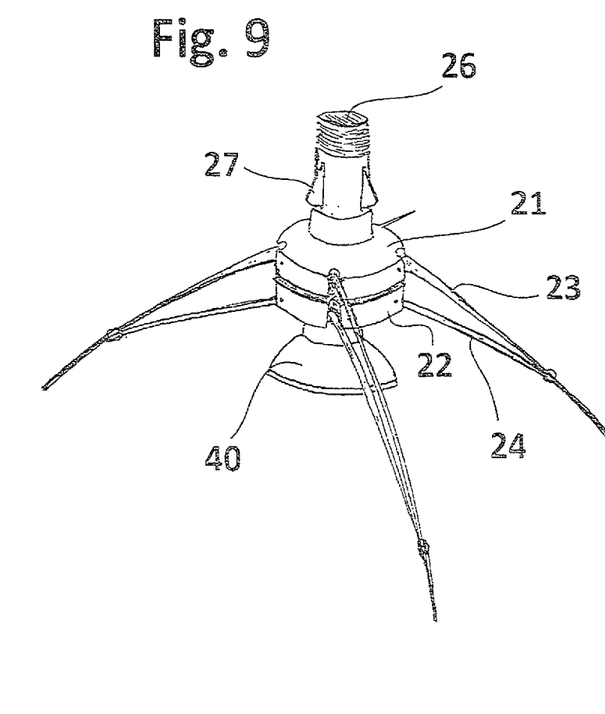
FIG. 9: Engaged lower and upper hubs other after containment structure deployment.

Generally, the apparatus 36 is an expandable and collapsible closed system, transparent, air and liquid impermeable space; an expandable and collapsible contained apparatus adapted to be erected in the field or where needed from a collapsed compacted form into an expanded form for handling, treating or processing an object or performing a task; or isolating, transporting and treating a person or an object. The apparatus extends into at least one direction generally outwardly from a collapsible packaged space to house a work field of full 62 or partial 63, 64, 65, 56 subject or field containment. One configuration example of this invention includes a contained miniature space (FIG. 4), and comprises a collapsible frame (FIG. 1, 14, 15), including a plurality of ribs pivoted at their upper ends to an upper hub or clevis member 21 providing a given final structure shape. At points spaced downwardly from their upper ends, each arm has pivoted thereto a radial stay member extending inwardly of the dome 24 to be pivoted to a lower hub or clevis 22. The upper clevis includes a central opening 51 to slide upwardly a central shaft 26, which is connected to the lower clevis 22. The lower clevis has fixed thereto the central shaft or rod 26 which protrudes upwardly and passes through upper clevis 21. The central shaft is pulled upwardly manually or mechanically to deploy and erect the collapsed containment structure outwardly (FIG. 2). The upper clevis will stop the upward movement of the lower clevis (FIG. 9), and locks 27 into each other by the passing of the central shaft 26 through the upper clevis 21. Spring-lock mechanism 27 is fixed toward the lower part of the central shaft 26. It latches when the lower clevis reaches the upper clevis and the latches 27 pass the upper clevis and expand outwardly and sit on the upper surface of the upper clevis 21. Latches 27 can be pushed inward to allow the hubs to be pushed apart to collapse the apparatus.

Figure 4:
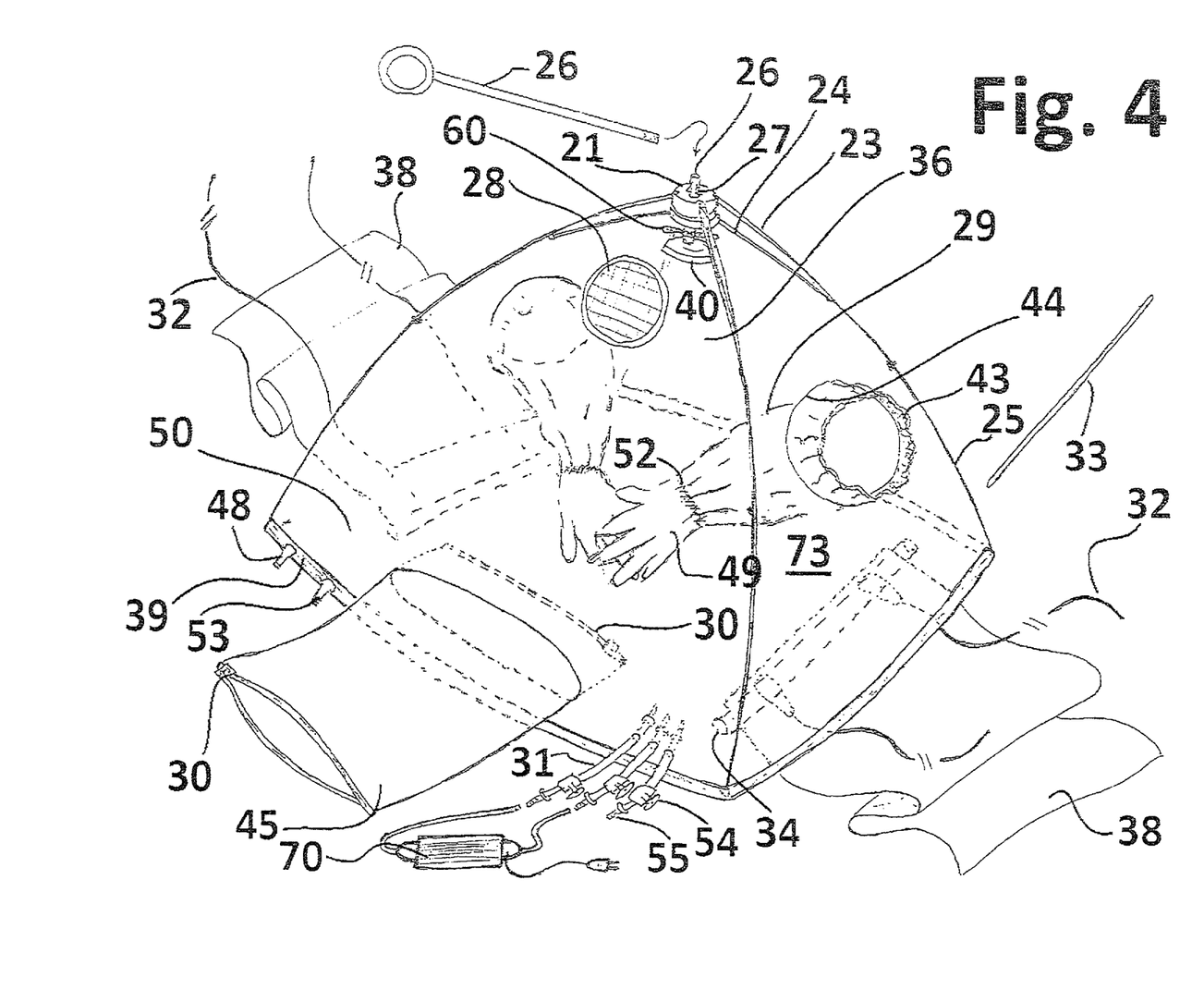
FIG. 4: General detailed view of the apparatus
Figures 5, 6, 7:
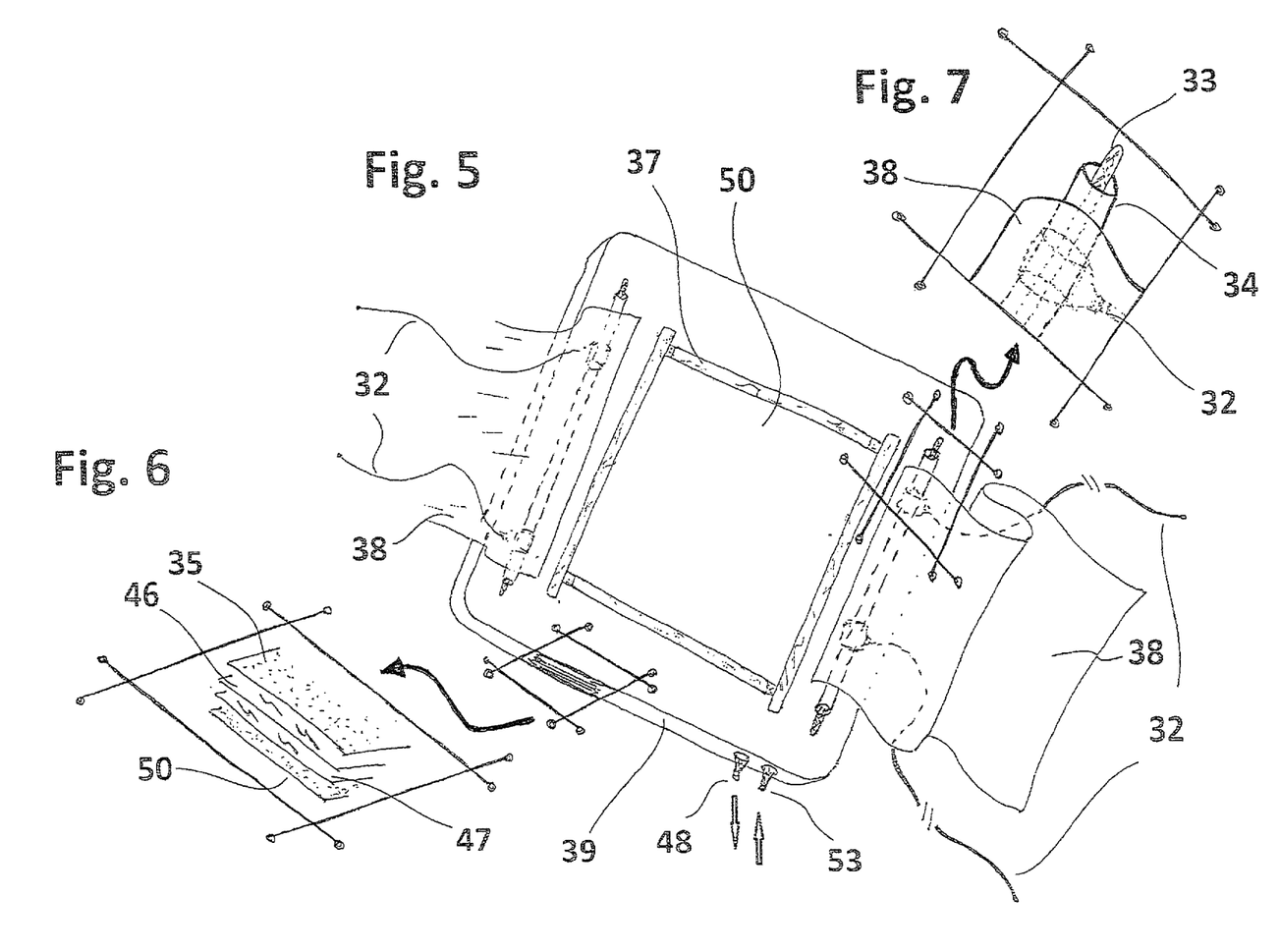
FIG. 5: General view of the bottom of the base of the apparatus
FIG. 6: Different layers of the bottom of the apparatus
FIG. 7: Enlarged view of the positioning of the flap drapes to the tubular channels and the stabilizing rod.
Figures 8A, 8B:
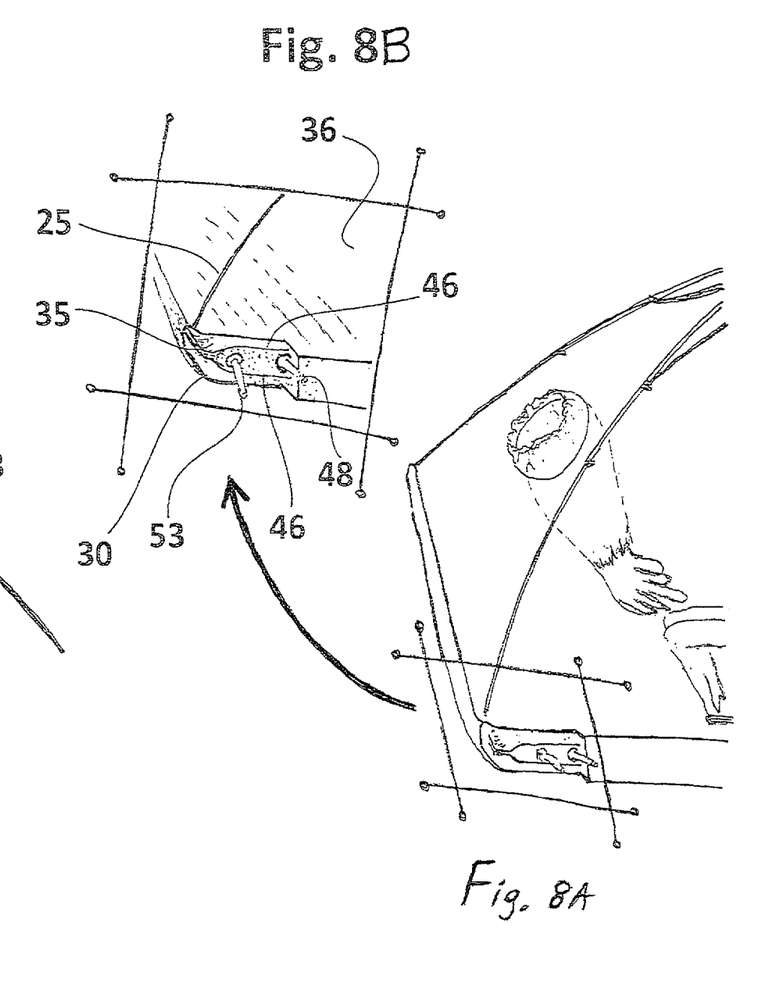
FIGS. 8A and 8B: Detailed cross-section of the base of the apparatus

The containment device general construction may be comprised of a metal or polymeric rib structure (FIG. 2). Each rib is comprised of an elongated lower section 25, which can be relatively flexible. The upper end of the lower section is pivotably connected at joint 41 to an upper section 23, which is pivoted to the upper clevis 21, and is relatively flexible and resilient so that the upper portions of the ribs conform to the shape of the canopy material forming the overall containment volume shape 36. An accordion-like embodiment may expand longitudinally to house larger objects. See FIGS. 15 and 16. In this case two spaced collapsible frames form the ends of the structure. They are connected together by hinged ribs 61 that form the top of the expanded structure. This example is deployed by pulling up on the two rings while also pulling them apart. The containment space (a dome), consists of an at least partially transparent (see through) polymeric canopy 73 of high transparency and strength and covers the ribbed containment space structure (FIG. 2) tightly to form a contained field. The contained field may or may not be sterile. Canopy 73 may consist of liquid, fog and glare repellent polymeric surface material. The collapsible structure may comprise a canopy made of transparent polymeric material with an integrated reinforcing fiber-based net 66, or may be reinforced by spaced fibers permanently attached to or within the transparent containment material 36. The canopy covers tightly when erected the containment volume frame from all directions (FIG. 4). The canopy material advantageously can include a complete floor portion base 50, which can be connected to the sidewalls of the canopy through connecting edge or seam 39. Advantageously, the ribs and stays of the frame are of extruded polymeric tubing or rods, or metal tubing or rods. The clevis members are molded from polymeric material or are metal, as are all of the pivotal connector members of the frame.

The invention may include one or more gloved-sleeves 29 connected outwardly to openings in the side of the canopy, with sealing elastic cuffs 43 to form a tight closure around the operator's arms. Inwardly, the other free ends of the sleeves terminate with gloved formation 49. A completely sealed and loosely connected inner diaphragm can be positioned at a wrist elastic region 52. The sleeves are tubular and openly connect outwardly to the surface of the canopy 44, with an elastic edged-curtain 43 to form a tight closure around the upper part of the operator arms or any other object. These polymeric sleeves may be modified and used to handle and manipulate partially an object 72 (FIG. 18) inside the apparatus without having direct physical contact between the operator's hands and the inner surfaces, objects or space of the apparatus.

One or more two-sided opening delivery (pass through) air-lock sleeves 45 can be connected to the surface of the canopy; with ends consisting of a closing zipper, Velcro® (hook and loop fastening materials) or other types of interlocking and sealing mechanisms 30, to close both ends of the sleeve outwardly and inwardly. Thus the sleeves act as air-locks. These sleeves are used to have controlled access to the inside and the outside of the apparatus. Sleeves with smaller ports are used to deliver or provide an access path for entry of devices such as scopes 57.

On one side of the canopy surface (typically the outside) there can be controlled flow mechanisms 54 (e.g., valves) for access tubes 31 passing through the canopy for fluid, mist 67, filtered or sterilized air, electrical cords 71 and other such supply or device needs 70, with couplings 55 providing connections between the outside and the inside of the apparatus. One tube can have a small bidirectional air flow filter 70 connected to a tube to inflate the containment volume or to suction air out or to provide certain gases.

By opening/cutting through the base 50 of the apparatus, a full access to the operated on field 63 can be achieved with partial subject containment and full field containment 63. The apparatus base 50 can have a continuous base surface connected to the downward end of the canopy surfaces 39, which will provide a closed system. Base 50 can be made of double polymeric sheet or layers of surgical absorbent drape materials 35, 46, 47, 50. Double polymeric sheets 46, 47 are sealed completely around the edges 39 and can enclose zigzag tubes 68 for circulating air or fluid to create a temperature controlled mattress with two simple in and out valves 48, 53. This removable air or fluid filled mattress will create a cushion to support the use of the apparatus for subjects placed inside the apparatus and can provide heat insulation. In addition, there can be an air filter 28 (e.g., a HEPA filter) fixed on the side of one of the canopy surfaces to provide filtered air to the dome if needed.

On the bottom of apparatus base 50 there can be surgical grade gel adhesive 37 to fix and seal the apparatus against the operated field or an object (e.g., a body part) 56. Parallel to two opposing sides of the adhesive 37, there may be two tubular tunnels 34 to house two apparatus-base stabilizer polymeric or metal rods 33 passing through the two tubular channels. The two tubular tunnels can also have two pair of ties 32. Each pair of ties may be fixed apart to each tubular tunnel and around the bars 33. Ties 32 will stabilize the base of the apparatus around the serviced object 56 by wrapping two flap drapes 38 around the serviced object 56, to contain and protect the integrity of the worked-on surface adhered to the bottom of the base 50 of the containment volume. The functions of the ties may also be accomplished with hook and loop type fasteners (e.g. Velcro® hook and loop fastening materials) or other mechanical fasteners.

At the bottom of the lower clevis 22, a light source 40 of any wave length can be configured with inner or outer source of power 71, to illuminate the inner field or to provide ultraviolet (UV), blue or infrared light within the unit. The light source may be connected to the bottom of the lower clevis, facing the inner space of the containment volume. Light source 40, such as UV, may have a removable shield 59 placed in front of it to prevent direct exposure of the patient or object to the light, but it will allow direct contact and circulation of the contained air within the space of the embodiment. A small fan 60 can be added to circulate the air within the interior space. On the other hand, an external sterilizer (UV, Ozonizer) may be added externally 70 to achieve the same purpose, with air circulated from the contained volume past the sterilizer and back into the contained volume. A fan may be used to aid in circulation of the air.

Figure 17:
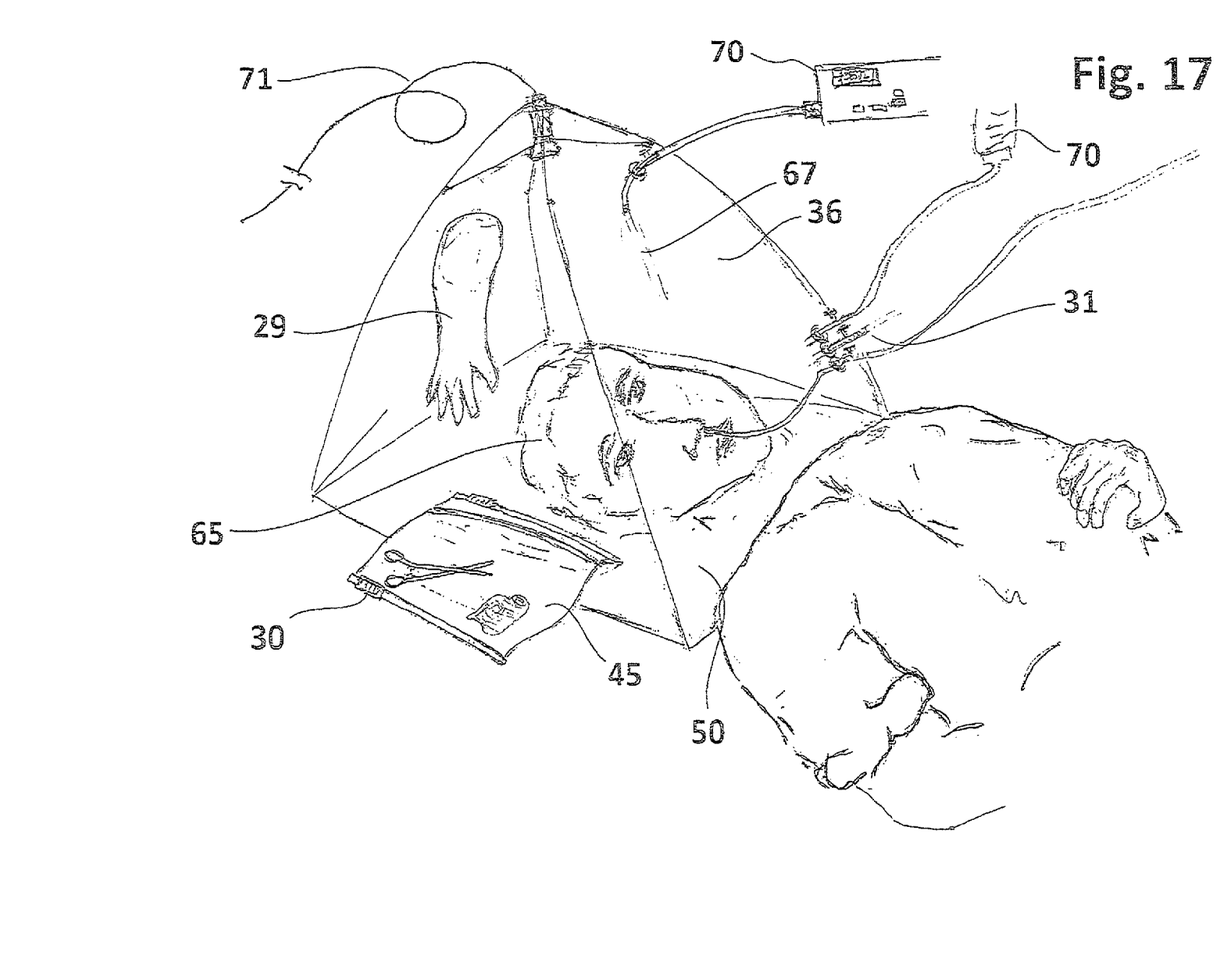
FIG. 17: Partial containment of subject's head through the base of the apparatus
Figure 18:
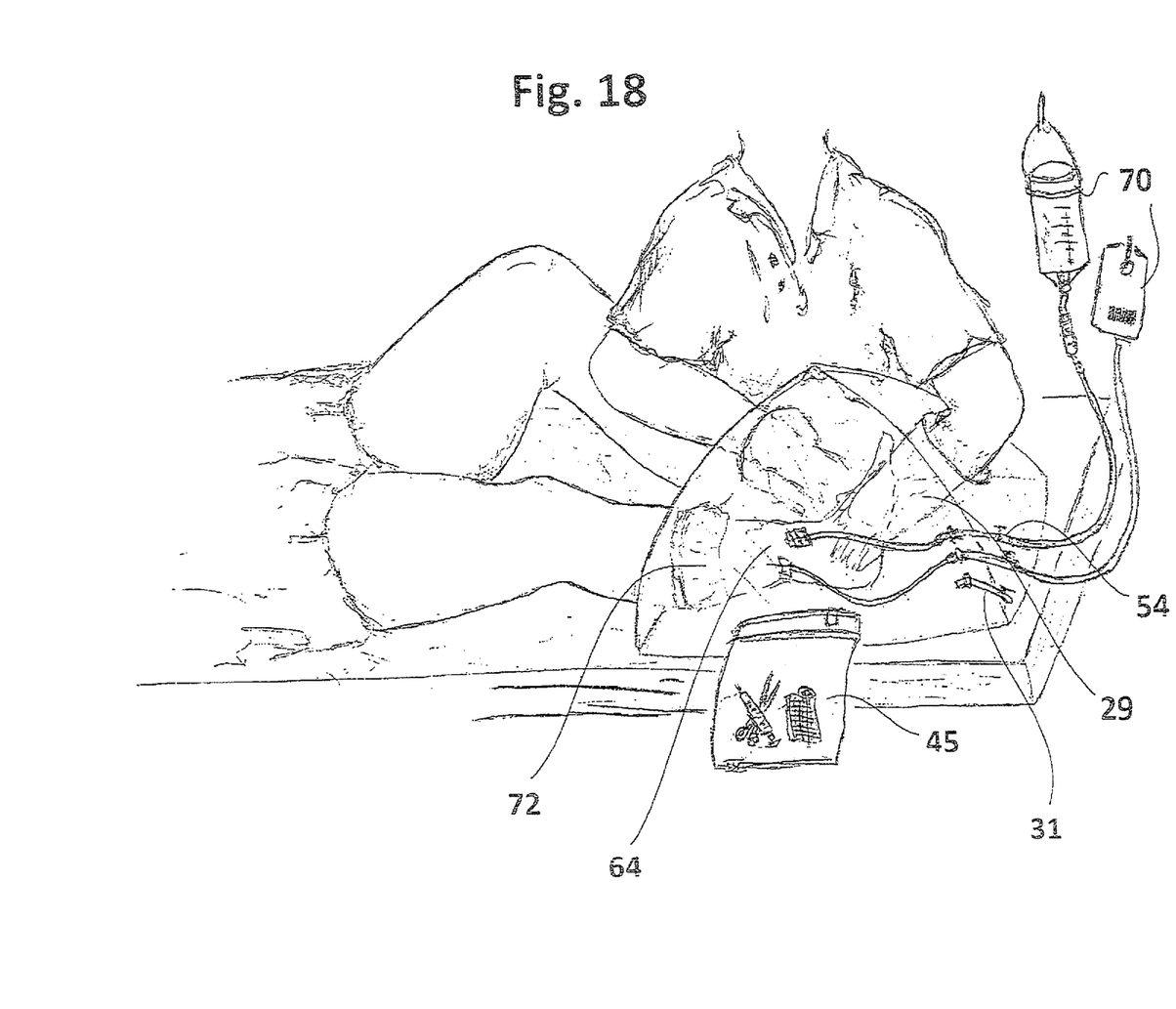
FIG. 18: Partial containment of subject's limb through a sleeve of the apparatus
Figure 19:
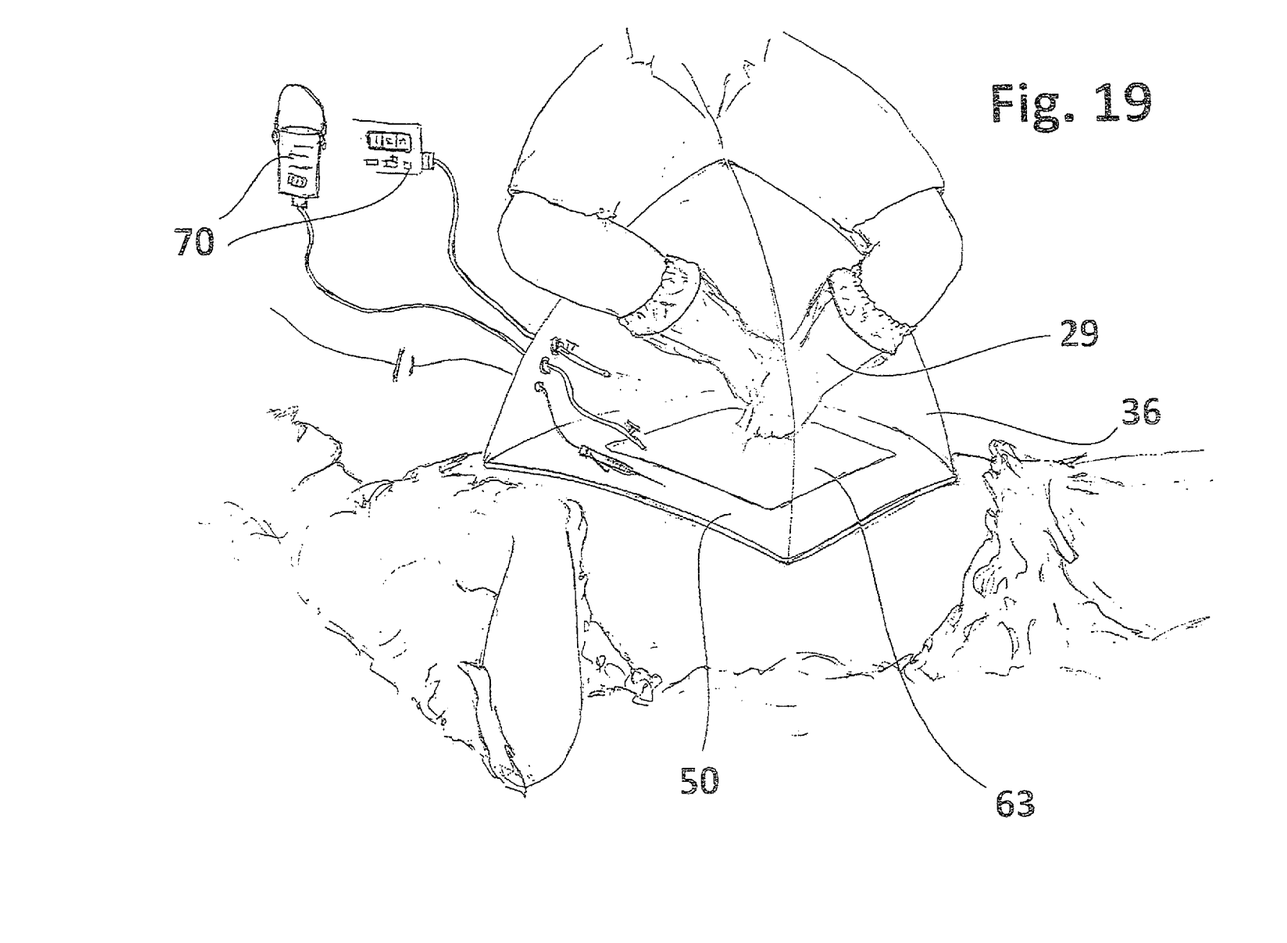
FIG. 19: Full exposure of the surgery field through the base of an injury site

This invention can be adapted for various applications, including but not limited to the following:

Partial Containment (FIGS. 17-19):

The apparatus can be used to conduct a wide array of procedures, surgeries or operations for human and non-human use, by placing the operator's hand into the apparatus gloves to get access to the worked-on (operated-on) site, and by opening/cutting through the base of the apparatus to reach the patient. Alternatively, partial parts of the patient (such as limbs) may be introduced into the interior of the apparatus (controlled space) through the air-lock sleeves. The operator's hands are isolated from, and do not directly contact, items within the contained and controlled space. This apparatus can be used in situations where no conventional medical establishment is available, such as in ambulatory and emergency services, third world countries, in areas of conflicts, rural areas, or in a regular clinical setting. This apparatus can also be applied for arthroscopy, endoscopy, and other procedures in an office setting instead of the use of a surgery room. In addition, the apparatus can be used for the treatment of burn victims and wounds or situations mandating a special contained environment and care. Examples of other situations include treatment and healing of skin graft donor sites, diabetic foot ulcers, amputation wounds, and other severe or chronic wounds. The device allows the introduction of various substances and/or control of the contained environment. The apparatus allows for the non-conventional approach of having the serviced subject (patient) and the operator outside the actual operating field, which negates the need for an aseptic room and operator's preparation, but it will give the operated-on site a high degree of containment and maintain a sterilized/aseptic field. The operator will reach the operated-on site through the gloved sleeves without direct contact. There will be very minimal or no effect or contact of the surrounding environment on the operation site when instruments or objects are delivered through the side sealable sleeves. In addition to the sterilizers, there can be positive air pressure maintained through a pressurized air-canister connected to the controlled flow access tubes, or negative pressure using a vacuum device. This apparatus can also be used to contain and clean any spills of any chemicals or biohazard materials, or for other situations were containment is required.

Figure 11:
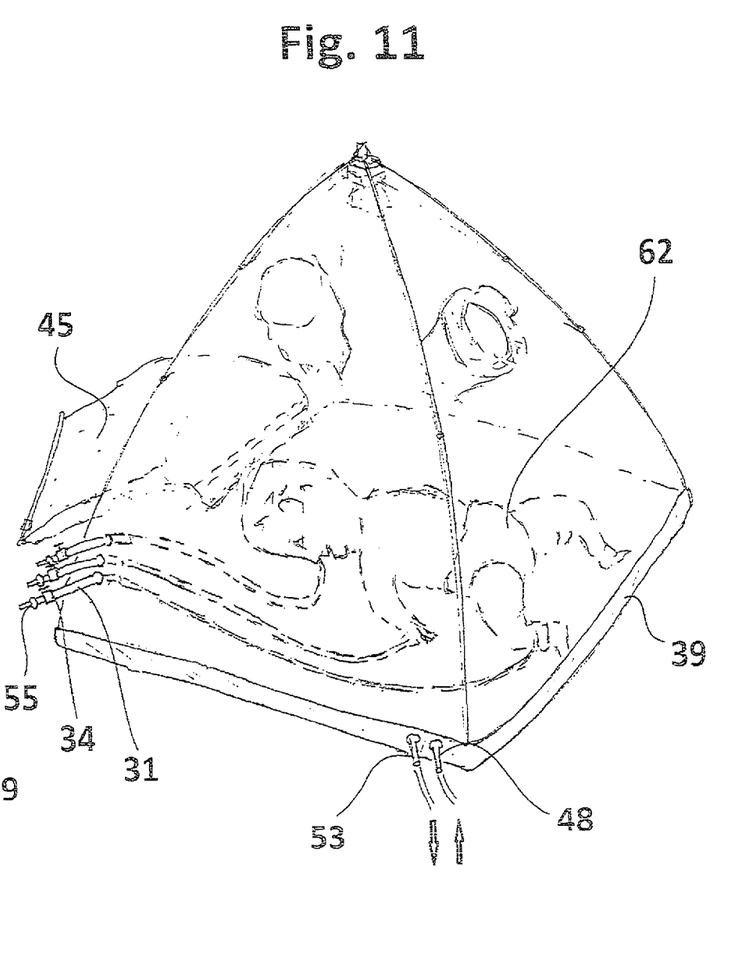
FIG. 11: Full subject containment use of apparatus
Figure 12:
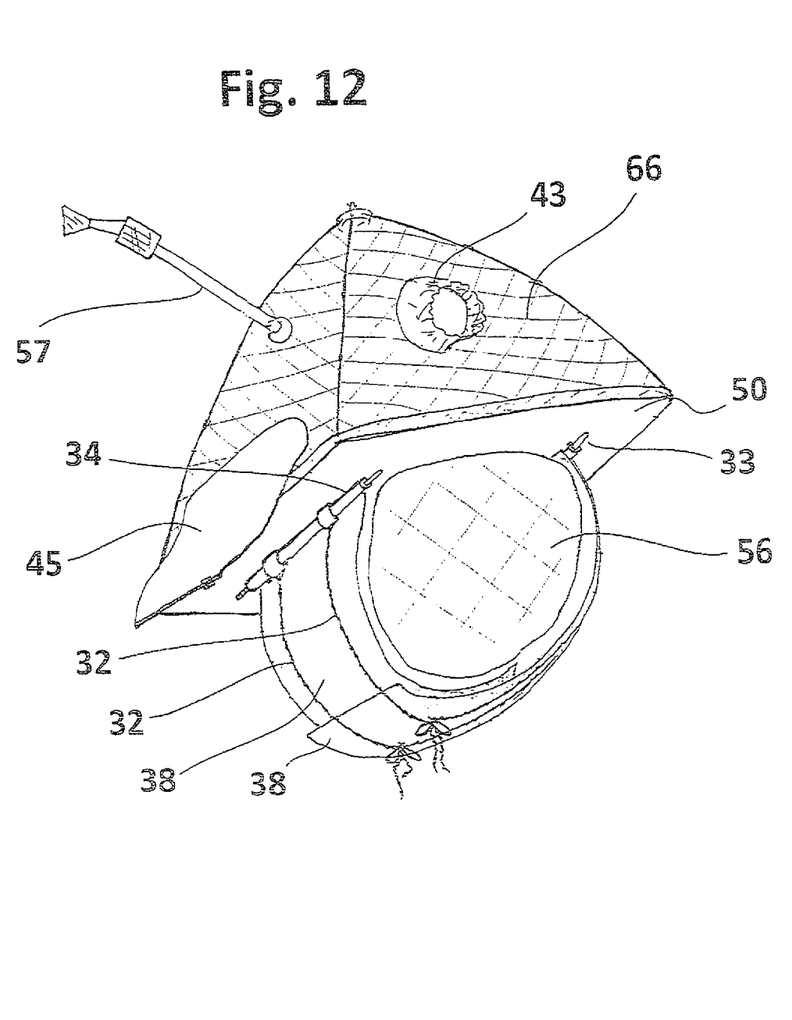
FIG. 12: Partial subject containment use of the apparatus
Figure 13:
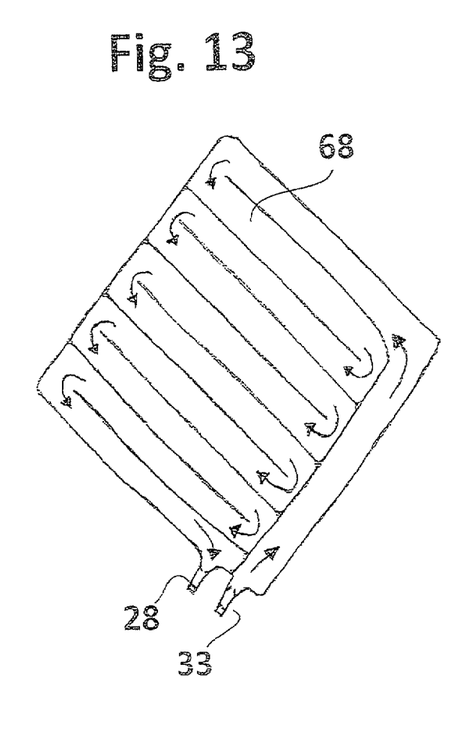
FIG. 13: Longitudinal cross-section of the dome base

Full Containment (FIG. 11):

The apparatus can also be used as a fully contained space for a wide variety of uses, in-vivo or in-vitro. The device may provide a sterilized/aseptic area for handling, testing and manipulating human subjects, other objects, biohazard agents, and chemicals placed within the contained space of the apparatus. In general, the agents are delivered through the sealable air-locked sleeves. To deliver any object inside the apparatus, unseal and open the outside portion of the sleeve, deliver the object to the inside of the sleeve, reseal the outside sleeve portion, then from inside the apparatus and by using the gloved sleeves unseal and open the inner sleeve portion and bring the object into the inner space of the apparatus. Positive air pressure from the air source can be maintained at all times to prevent contamination, in addition to the use of a sterilizer if desired.

The apparatus can be used in the field of preterm born infants or for small animals as an incubator or treatment station with minor changes to the basic platform; that is, like the addition of light, heat, humidity, oxygen, etc. One sleeve can be made large enough to deliver thereto large objects, with air-lock capability. The apparatus can be used for disposable or longer term use. This contained and sealed system will provide the operator and the surrounding environment complete protection and vice versa, and safe disposal of biological, medical, and/or other potentially hazardous materials with significantly lower cost than current methods.

The apparatus can be used as a portable clean room in many other industries, such as delicate assembly or handling of electronics, among other uses whenever clean, aseptic or sterile environment is needed.

The apparatus can be used when and wherever a skilled operator is available, but there is lack of availability of the appropriate physical setting and space. It is flexible and versatile by the simplicity of adding useful features like a sterilizer, light, suction, fluid delivery, oxygen/air, etc. The apparatus is small, light weight, cost effective, dramatically reduces procedural costs, increases patient safety, and saves time.

APPENDIX

List of Numbered Parts in the Drawings

21 Upper clevis (upper hub)
22 Lower clevis (lower hub)
23 Upper radial member of the canopy frame ribs structure
24 Short arm connected the lower clevis (hub) and the upper rib radial member of the canopy frame
25 Lower radial member of the canopy frame ribs structure
26 Central shaft
27 Mechanism to lock lower and upper clevis (hub)
28 HEPA and such filter
29 Gloved sleeve
30 Sleeve interlocking/sealing mechanism
31 Tube with controlled access between the interior and exterior environment
32 Base ties
33 Base tubular tunnel bar
34 Base tubular tunnel
Base absorbent layer material
36 The apparatus, contained environment, canopy, dome
37 Base adhesive
38 Base flap drape 39 Connecting edge between the canopy and the lower section floor (base)
Light source
41 Folding joint mechanism between the upper (23) and lower (25)
43 Outer elastic cuff of the sleeve
44 Outward sleeve and canopy connection
45 Air-lock sleeve
46 Base non-absorbent layer material
47 Base non-absorbent layer material
48 Base valve
49 Glove of the lower sleeve portion
50 The base of the apparatus
51 Central opening of the upper clevis (hub) for sliding in the central shaft
52 Diaphragm to, and wrist elastic of, the lower portion of the sleeve
53 Base valve
54 Controlled access valve between the exterior and interior contained environment
55 Tube coupling
56 Partial subject containment with full field containment
57 Sleeve port for endoscopes and such
59 Light removable shield
60 Circulating air fan
61 Accordion-like mechanism bare members
62 Full subject containment
63 Partial subject containment with full field containment
64 Partial subject containment with full field containment
65 Partial subject containment with full field containment
66 Canopy reinforcing net
67 Introduced fluids
68 Base zigzag heating/cooling system (tubes)
70 Exterior supply devices (gases, sterility, suction, etc.)
71 Supply cords
72 Air-locked sleeves for partial subject containment
73 Canopy

What is claimed is:

1. An apparatus for containment of a subject's head, the apparatus comprising:
   a. a collapsible frame configured to move between an expanded configuration and a collapsible configuration; and
   b. a flexible canopy connected to the collapsible frame, the flexible canopy comprising a plurality of sidewalls and a base, the base of the flexible canopy configured to comprise an entry for insertion of a subject's head and to seal the canopy around the perimeter of the subject's neck to form a containment space around the subject's head when the collapsible frame is in the expanded configuration, said sidewalls having at least one port allowing for gas or fluid communication between the containment space and an exterior source and at least one bi-directional air-lock sleeve which comprises a sealing mechanism at each end of the sleeve that allows the sleeve to be selectively opened and closed at each end of the sleeve, and wherein the flexible canopy is at least in part transparent,
   wherein the collapsible frame, when it is in the expanded configuration, causes the flexible canopy to form a contained microenvironment around the subject's head.

2. The apparatus of claim 1, wherein the canopy is made at least in part of a polymeric material.

3. The apparatus of claim 1, wherein the base comprises an outer layer that is impervious to fluids, and at least one layer inside of the outer layer that is constructed and arranged to absorb fluids.

4. The apparatus of claim 1, further comprising one or more gloved sleeves coupled to at least one of the plurality of sidewalls and extending into the containment space, the gloved sleeves sized and shaped to accept a hand and an arm of a person.

5. The apparatus of claim 1, further comprising a sleeve comprising an elastic cuff that forms a tight closure around an operator's arm, wherein the sleeve can be open or with gloves.

6. The apparatus of claim 1, further comprising a reinforcement structure for the canopy that is either on or in the canopy.

7. The apparatus of claim 1, wherein the canopy has at least one layer that is impervious to fluids.

8. The apparatus of claim 1, where the at least one port is used for delivery of any one of: a gas, a liquid or a mist into the containment space.

9. The apparatus of claim 1, wherein the base comprises a double layer.

10. The apparatus of claim 1, further comprising an air filter in at least one sidewall.

11. The apparatus of claim 10, wherein the filter is a HEPA filter.

12. The apparatus of claim 10, wherein the air filter is connected to an internal or external sterilization device.

13. The apparatus of claim 12, wherein the internal sterilization device is a UV light source.

14. The apparatus of claim 12, wherein the external sterilization device is a UV light source or ozonizer, or device enabling germicidal irradiation.

15. The apparatus of claim 1, wherein the containment space is configured to have a positive or negative air pressure.

16. A method to limit exposure to airborne contaminants or biological hazards released from a subject, the method comprising placing the apparatus of claim 1 over a subject's head, wherein the subject is at risk of releasing an airborne contaminant or biological hazard.

17. The apparatus of claim 1, further comprising a fan to circulate air in the containment space, wherein the fan is attached to the collapsible frame.

* * * * *